(12) United States Patent
Lee

(10) Patent No.: US 10,806,233 B2
(45) Date of Patent: Oct. 20, 2020

(54) MASCARA COMPOSITION AND METHOD

(71) Applicant: ELC MANAGEMENT LLC, Melville, NY (US)

(72) Inventor: Wilson A. Lee, Hauppauge, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 16/049,928

(22) Filed: Jul. 31, 2018

(65) Prior Publication Data

US 2019/0014883 A1 Jan. 17, 2019

Related U.S. Application Data

(63) Continuation-in-part of application No. 15/354,730, filed on Nov. 17, 2016, now Pat. No. 10,064,806.
(Continued)

(51) Int. Cl.
*A61K 8/11* (2006.01)
*A61Q 1/10* (2006.01)
(Continued)

(52) U.S. Cl.
CPC .......... *A45D 40/267* (2013.01); *A45D 33/00* (2013.01); *A61K 8/027* (2013.01); *A61K 8/11* (2013.01); *A61K 8/19* (2013.01); *A61K 8/25* (2013.01); *A61K 8/416* (2013.01); *A61K 8/585* (2013.01); *A61K 8/64* (2013.01); *A61K 8/731* (2013.01); *A61K 8/736* (2013.01); *A61K 8/817* (2013.01); *A61K 8/8141* (2013.01); *A61K 8/8147* (2013.01); *A61K 8/8152* (2013.01); *A61K 8/8182* (2013.01); *A61K 8/87* (2013.01); *A61K 8/88* (2013.01); *A61Q 1/10* (2013.01); *A45D 2033/001* (2013.01); *A45D 2200/202* (2013.01);
(Continued)

(58) Field of Classification Search
None
See application file for complete search history.

(56) References Cited

U.S. PATENT DOCUMENTS 3,215,724 A 11/1965 Strobel et al.
3,439,088 A 4/1969 Edman
(Continued)

FOREIGN PATENT DOCUMENTS

EP 1407754 4/2004
EP 2209399 A2 * 7/2010 ........... A45D 40/267
(Continued)

OTHER PUBLICATIONS

Hauser, Peter J.; http://www.textileworld.com/Issues/2000/October/ Textile_News/Cationic_Pretreatments_Of_Cotton; Textile News; Fiber treatments before dyeing reduces environmental pollutants, increases dye affinity; Textile World—Cationic Pretreatments of Cotton; pp. 1-3; Nov. 2015.
(Continued)

*Primary Examiner* — Ernst V Arnold
(74) *Attorney, Agent, or Firm* — Tiffany A. Johnson

(57) ABSTRACT

Cationically-charged particulates and compositions containing the cationically-charged particulates for application to keratinous materials are provided. Methods of preparing the cationically-charged particulates are also disclosed. Methods of increasing the cationic charge on particulates are also provided.

15 Claims, 4 Drawing Sheets

Related U.S. Application Data

(60) Provisional application No. 62/256,276, filed on Nov. 17, 2015.

(51) Int. Cl.

| | | |
|---|---|---|
| *A45D 40/26* | (2006.01) |
| *A61K 8/81* | (2006.01) |
| *A45D 33/00* | (2006.01) |
| *A61K 8/02* | (2006.01) |
| *A61K 8/88* | (2006.01) |
| *A61K 8/73* | (2006.01) |
| *A61K 8/87* | (2006.01) |
| *A61K 8/41* | (2006.01) |
| *A61K 8/58* | (2006.01) |
| *A61K 8/25* | (2006.01) |
| *A61K 8/19* | (2006.01) |
| *A61K 8/64* | (2006.01) |

(52) U.S. Cl.
CPC .... *A61K 2800/623* (2013.01); *A61K 2800/87* (2013.01)

(56) References Cited

U.S. PATENT DOCUMENTS

| | | | |
|---|---|---|---|
| 3,781,417 A | 12/1973 | Welters et al. | |
| 3,818,105 A | 6/1974 | Coopersmith et al. | |
| 4,677,152 A | 6/1987 | Allen et al. | |
| 4,702,844 A | 10/1987 | Flesher et al. | |
| 4,803,067 A | 2/1989 | Brunetta et al. | |
| 4,970,252 A | 11/1990 | Sakuta et al. | |
| 5,118,496 A | 6/1992 | Herstein | |
| 5,183,588 A | 2/1993 | Salerno et al. | |
| 5,183,589 A | 2/1993 | Brunetta et al. | |
| 5,236,986 A | 8/1993 | Sakuta | |
| 5,412,004 A | 5/1995 | Tachibana et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |
| 5,858,338 A | 1/1999 | Piot et al. | |
| 6,534,044 B1 | 3/2003 | Wada et al. | |
| 6,955,805 B2 | 10/2005 | Shah et al. | |
| 7,914,220 B2 * | 3/2011 | Neuner | A45D 40/267 401/122 |
| 7,977,288 B2 | 7/2011 | SenGupta | |
| 2002/0192250 A1 | 12/2002 | Chevalier et al. | |
| 2003/0127209 A1 | 7/2003 | Sandberg et al. | |
| 2005/0100806 A1 | 5/2005 | Hongo et al. | |
| 2005/0196363 A1 | 9/2005 | Horino | |
| 2006/0034875 A1 | 2/2006 | Nakanishi et al. | |
| 2006/0159642 A1 * | 7/2006 | Hanna | A61K 8/8141 424/70.7 |
| 2006/0172909 A1 | 8/2006 | Schmiedel et al. | |
| 2006/0177383 A1 | 8/2006 | Gebreselassie et al. | |
| 2007/0078071 A1 | 4/2007 | Lee et al. | |
| 2008/0292668 A1 | 11/2008 | Baars et al. | |
| 2010/0303913 A1 | 12/2010 | Gheith et al. | |
| 2012/0003287 A1 | 1/2012 | Schlossman et al. | |
| 2014/0086964 A1 | 3/2014 | Finjan et al. | |
| 2015/0209244 A1 | 7/2015 | Cohen et al. | |
| 2015/0272840 A1 | 10/2015 | Liu et al. | |
| 2016/0122568 A1 | 5/2016 | Catchmark et al. | |
| 2017/0135937 A1 | 5/2017 | Lee | |
| 2017/0135939 A1 | 5/2017 | Lee | |
| 2017/0135940 A1 | 5/2017 | Lee | |

FOREIGN PATENT DOCUMENTS

| | | | |
|---|---|---|---|
| JP | 61-18708 | 1/1986 | |
| JP | 2000-154116 | 6/2000 | |
| JP | 2002-275032 | 9/2002 | |
| JP | 2005-247720 | 9/2005 | |
| JP | 2007-527930 | 10/2007 | |
| JP | 2009-235029 | 10/2009 | |
| JP | 2010-116373 | 5/2010 | |
| JP | 2014-162920 | 9/2014 | |
| JP | 2015-180678 | 10/2015 | |
| JP | 2015-532925 | 11/2015 | |
| JP | 2018-533636 | 11/2018 | |
| JP | 2018-533637 | 11/2018 | |
| JP | 2018-535264 | 11/2018 | |
| JP | 2018-587531 | 12/2018 | |
| KR | 10-2009-0056396 | 6/2009 | |
| KR | 10-2010-0040048 | 4/2010 | |
| KR | 10-1248973 | 4/2013 | |
| KR | 10-2014-0049883 | 4/2014 | |
| KR | 10-2018-0067728 | 6/2018 | |
| KR | 10-2018-0075676 | 7/2018 | |
| WO | WO-2004/024798 | 3/2004 | |
| WO | WO-2008/005693 | 1/2008 | |
| WO | WO-2009/100464 | 8/2009 | |
| WO | WO-2011/162967 | 12/2011 | |
| WO | WO-2012158857 A1 * | 11/2012 | ............. A61K 8/375 |
| WO | WO-2014/064121 | 5/2014 | |
| WO | WO-2017/087718 | 5/2017 | |

OTHER PUBLICATIONS

Ko, et al.; The effect of cationic polymer treatment on adhesion of iron oxide to eyelashes; Journal of Cosmetic Science.; vol. 60; Issue 6; pp. 617-625; Nov./Dec. 2009.

PCT Int'l Search Report; Int'l Application No. PCT/US2016/062600; Completion Date: Mar. 31, 2017; dated Mar. 31, 2017.

PCT Int'l Search Report; Int'l Application No. PCT/US2016/062605; Completion Date: Mar. 31, 2017; dated Mar. 31, 2017.

PCT Int'l Search Report; Int'l Application No. PCT/US2016/062609; Completion Date: Mar. 31, 2017; dated Mar. 31, 2017.

PCT Int'l Search Report; Int'l Application No. PCT/US2016/062611; Completion Date: Mar. 31, 2017; dated Mar. 31, 2017.

PCT Written Opin of the Int'l Searching Auth; Int'l Application No. PCT/US2016/062600; Completion Date: Mar. 31, 2017; dated Mar. 31, 2017.

PCT Written Opin of the Int'l Searching Auth; Int'l Application No. PCT/US2016/062605; Completion Date: Nov. 30, 2015; dated Dec. 28, 2015.

PCT Written Opin of the Int'l Searching Auth; Int'l Application No. PCT/US2016/062609; Completion Date: Mar. 31, 2017; dated Mar. 31, 2017.

PCT Written Opin of the Int'l Searching Auth; Int'l Application No. PCT/US2016/062611; Completion Date: Mar. 31, 2017; dated Mar. 31, 2017.

Vitis Vinifera (Grape) Ingredients as Used in Cosmetics; Scientific Literature Review; Feb. 2012. (29 pp.).

Supplementary European Search Report; EP16867165; Completion Date: Mar. 20, 2019; dated Apr. 5, 2019.

Supplementary European Search Report; EP16867168; Completion Date: Mar. 28, 2019; dated Apr. 5, 2019.

Supplementary European Search Report; EP16867170; Completion Date: Mar. 21, 2019; dated Apr. 5, 2019.

Supplementary European Search Report; EP16867172; Completion Date: Mar. 22, 2019; dated Apr. 5, 2019.

* cited by examiner

MASCARA COMPOSITION AND METHOD

FIELD OF THE INVENTION

The invention relates to novel cosmetic compositions suitable for application to keratinous materials, such as eyelashes, eyebrows and hair, and to methods of making the compositions. More specifically, the invention relates to fibers or other particulates which have been uniformly coated with a cationically-charged material, and to compositions containing the coated particulates.

BACKGROUND OF THE INVENTION

Consumers desiring longer and thicker eyelashes have traditionally resorted to the use of false eyelashes which are applied with glue to natural eyelashes or to costly lash extensions. As an alternative, various mascara products have been popular. Nevertheless, some eyelashes are just too sparse for just any type of volumizing mascara to make them look more dramatic. On the other hand, even women with a great eyelash fringe may desire a more intense result than may be achieved using their favorite mascara. Features that mascara products are expected to have include the ability to darken, thicken and lengthen the eyelashes so as to achieve eyelashes having a fuller appearance without clumping or flaking off. In addition, it is desirable that the product be water- and/or smudge-resistant yet not be difficult to remove. The cosmetic industry has responded to this demand by providing mascara compositions containing fibers, waxes, and/or bulking or filler agents; however, there are limitations on the amount of such ingredients which can be added to the formulations without reducing processibility of the formula, or interfering both with loading a brush with product and delivering product from the brush to the eyelashes. Also commercially available are fibers for application to mascara-coated eyelashes. A disadvantage associated with such fibers is that when drawn out of a receptacle, the fibers tend to pick up negative charges from the atmosphere which causes them to become statically-charged and to repel one another and fly about. To deal with this issue, fibers have also been formulated into gel products. Nevertheless, fibers in such products often do not sufficiently adhere to the eyelashes upon application or even after dry down but tend to flake off onto the face and into the eyes causing irritation.

There continues to be a need to formulate a fiber-containing composition which will better adhere to the eyelashes, eyebrows or hair to achieve the desired improvements in volume and/or length, and without the aforementioned disadvantages associated with conventional products.

SUMMARY OF THE INVENTION

Embodiments herein relate to cationically-charged particulates, and to compositions comprising the cationically-charged particulates, for application to negatively charged keratinous materials, such as eyelashes, eyebrows and hair. The particulates are provided with the cationic charge by encapsulation with a coating comprising a cationically-charged material. The cationically-charged particulates are optionally coated with a film-former finish material to further seal the cationically-charged coating to the particulates and to render the particulates hydrophobic. The film-former material may be hydrophilic or hydrophobic, but is hydrophobic on dry-down.

Embodiments herein also relate to methods of preparing the cationically-charged particulates and particulate-containing cosmetic compositions.

Embodiments herein further provide methods of increasing the cationic charge of particulates. The methods include coating a rod with cationically charged particulates, contacting the rod with a surface at least once to generate a static charge, and transferring the static charge to the cationically charged particulates on contact.

DETAILED DESCRIPTION OF THE INVENTION

Figure 1:
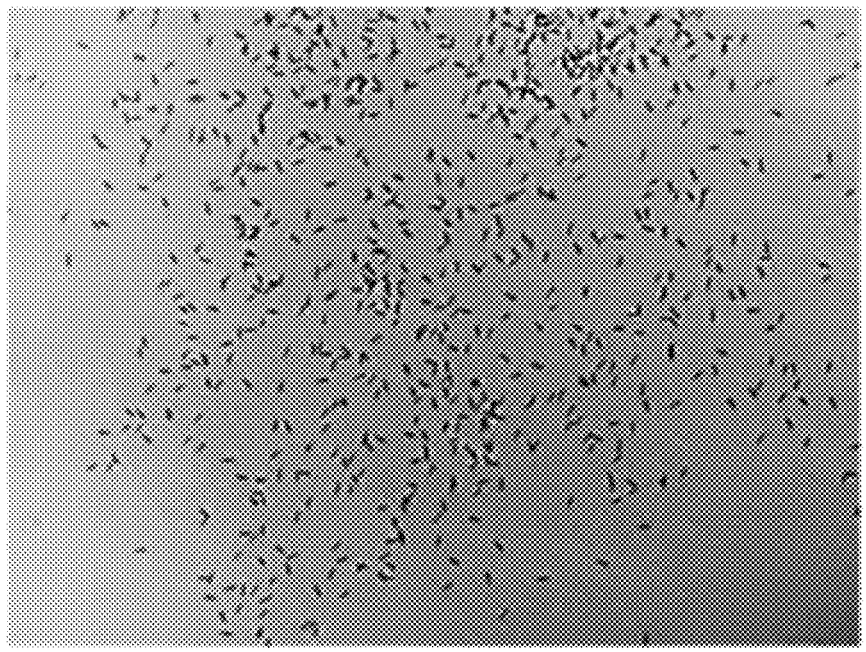
FIG. 1 depicts a sheet of paper onto which statically-charged fibers have scattered from a brush withdrawn from a vial of the virgin fibers.

The use of coatings on the surfaces of particles has been known for more than forty years in the personal care industry. Such coatings are widely used to encapsulate tablets so that they are completely and evenly coated with a coating material. The benefits of a coated tablet include the ability, upon degradation of the coating, to absorb materials from an environment; or to release materials, such as active agents disposed in a matrix of the coating, into an environment. As coatings may possess porosity, as in the case of a zeolite, such coating do not require release in order to render absorption or release of a material into or out of the matrix of the coating. In cases such as these, very high selectivity may be obtained by using properly tuned pore characteristics.

The surface treatment of pigments has also been used to improve the ability of incorporating them into cosmetic formulations. For example, pigments coated with different types of silicones are commercially available and when used as cosmetic pigments in formulations the coating facilitates the incorporation of the pigment into hydrophobic formulations whereas the untreated pigment would generally remain poorly dispersed. Other pigments may be coated with fluorocarbon polymers to improve their adhesive power while also forming a film upon application. Still other pigments may coated with natural polymers such as proteins, for example collagen. These types of coatings do not demonstrate a waterproofing property but the natural proteins do enhance ease of pigment dispersion into the hydrophilic phase of the cosmetic formulation and may be used to introduce a cationic charges into the formulations. Although protein-coated pigment introduced into the hydrophilic phase demonstrates better binding on dry down, such coated pigments have not been shown to adhere sufficiently to skin. Additionally, dispersed proteins tends to separate out from such formulations during manufacturing.

A commonly used material for an encapsulation coating is silicone polymer. There have been many efforts to improve the adhesion of particulates to keratinous materials by coating the particulates with silicones. Silicone polymers have been widely used because they possess two advantageous properties: biocompatibility and permeability to gases and small molecules. Advantages for use in cosmetics include their contribution to waterproofing or water-resistance property, feel, and shine, and they also are compatible with most oil phases of a base formulation. Nevertheless, the use of silicones for coating particulates has its drawbacks, including excessive shine and incompatibility with water and water-soluble ingredients.

Nevertheless, prior to the present invention, it had not been known to coat particulates with a cationically-charged material for formulation into cosmetic compositions for application to keratinous materials. Dry, treated particulates of the invention demonstrate greater adhesion to negatively-charged eyelashes, eyebrows and hair compared with untreated particulates. The dry, treated particulates may also be incorporated into volumizing mascara, eyebrow filler and hair filler formulations to provide such formulations with superior adhesion to negatively charged eyelashes, eyebrows and hair.

Keratinous materials have an anionic charge of about −24 mV. The surface of particulates, for example, fibers, treated according to the present invention, will typically have a net cationic charge in the range of from about 0.1 mV to about 400 mV which will facilitate their adherence to the keratinous materials. A net cationic charge of greater than about 400 mV would be expected to create dramatic flyaway of the fibers (due to repellent forces between fibers) when pulling a brush loaded with dry, treated particulates out of a container holding the dry treated particulates. When incorporated into a base formulation, treated particulates having a net cationic charge of greater than about 400 mV would tend to be tacky and agglomerate in the container. Particulates with a net cationic charge of less than about 0.1 mV would not be expected to adhere sufficiently to eyelashes, eyebrows and/or hair, whether the particulates are used dry or incorporated into a base formulation.

In accordance with compositions and methods of the present invention, the dry, treated particulates have a net cationic charge, measured as the zeta potential, in the range of from about 0.1 mV to about 400 mV, such as from about 24 mV to about 200 mV, for example, in the range of from about 60 mV to about 150 mV.

The cationic charge is imparted to the particulates by means of at least one coating containing a cationically-charged material. In some embodiments of the present invention, the coating comprises a natural or synthetic cationic compound dispersed in an aqueous-based medium, preferably a water and alcohol medium, to facilitate evaporation of the medium and drying of the particulates. One class of such compounds includes cationically charge-modified polymers where the cationic groups enhance the polymer's substantivity to anionic substrates, such as keratinous materials. Natural cationically charge-modified polymers may be derived from various animal and plant sources including guar gum, cellulose, proteins, polypeptides, chitosan, lanolin, and starches and combinations thereof. Synthetic compounds include those with quaternary ammonium functional groups, for example, cationic polymers, such as polyquaternium-4, polyquaternium-5, polyquaternium-6, polyquaternium-10, polyquaternium-39, polyquaternium-44, polyquaternium-46, quaternary ammonium salts, including, distearyldimonium chloride, cinnamidopropyltrimonium chloride, cetrimonium chloride, and guar hydroxypropyltrimonium chloride, and combinations of any two or more cationically-charged materials. A cationic coating comprising polyquaternium-6 is particularly preferred for its charge density. A further example of a cationically-charged coating useful in the present invention is powdered iron (FeO).

Particulates coated with the cationically-charged coating may optionally, but not necessarily, be further encapsulated with a film-former finish. The film former aids in the adhesion of the cationically-charged material to the particulate surfaces, and additionally can be configured to impart hydrophobicity to the particulate surfaces. So as not to hinder the film former from binding to the cationically-charged surfaces of the particulates, the cationically-charged coating typically comprises water in an amount of between about 0.01 and 5.00 percent by weight after drying which limits their charge density.

The film former coating preferably comprises at least one water-soluble or water-dispersible polymer having a surface tension of less than about 75γ, and preferably in the range of from about 20γ to about 65γ. The polymers preferably exhibit good water-resistance, adhesion and flexibility on dry down. Film forming polymers useful for encapsulating the cationically coated particulates, may be hydrophilic or hydrophobic, but are hydrophobic when dry. Examples of suitable polymers, include, but are not limited to, silicones, such as methyltrimethicone, trimethylsiloxysilicate, and dimethicone, dimethicone and trimethylsiloxysilicate, and the like; acrylates polymers and copolymers, such as Syntran PC 5775, Syntran PC 5776, Avalure AC-120, Daitosol 5000AD, Daitosol 5000SJ; Daitosol U9-40, Vinylsol 214oL Vinylsol 1086 WP; polyvinylpyrrolidone (PVP) derivatives, such as PVP K-30, PVP/VA E-635, PVP/VA W-735; polyurethanes, such as Luviset P.U.R., Giovarez P-0580, and Baycusan C 1004; polyvinyl amines and polyvinyl acetates. Non-polymeric film-former finishes may include, but are not limited to, esters, such as sucrose acetate isobutyrate, which may be used alone, or in combination with any of the aforementioned polymers.

In one preferred embodiment of the invention, the film-former coating is a silicone polymer blend. A film former solution may contain, for example, dimethicone and trimethylsiloxysiliate in trisiloxane. When dried, this coating creates a high contact angle with the particulates which renders the treated particulates particularly compatible with water-in-oil and water-in-silicone systems. In another preferred mbodiment, a film-former solution contains dimethicone, trimethylsiloxysilicate and polyglyceryl-3 disiloxane dimethicone in trisiloxane. When dried, this film former creates a lesser contact angles with particulates. It possesses hydrophilic (i.e., polyglycerin) side chains which enhance the compatibility of the treated particulates in oil-in-water and silicone-in-water systems.

The amount of film former used should be an amount sufficient to encapsulate the cationically charged particulates and render them hydrophobic, but not be so great as to decrease the net cationic charge of the particulates to a level which would reduce the level of cationic charge below a value useful in the present invention. In the case where the treated fibers or a formulation containing the treated fibers, are used on the eyelashes, it is preferred that the cationically-charged fibers be encapsulated in film former, since oil in the skin around the eyes may dissolve the cationic material on the fibers. The dissolved cationic material may make contact with and irritate the eyes. The film former encapsulation is not necessary where the fibers or a formulation containing the fibers will be used on the eyebrows or in the hair.

Additional coatings may be deposited on the particulates prior to the final film former finish. Such additional coatings may be liquid or solid, and may deposit anionic material, cationic material, or both. In some embodiments of the invention, the additional coatings contain proteins, peptides, or a combination thereof. An intervening anionic coating may be used to balance a high cationic charge of particulates coated with the initial cationically charged coating. The net cationic charge may also be modified with the film former coating. A thicker the film former coating may also be used to reduce a high cationic charge. The coated particulates, however, carry a net final charge of from about 0.1 to about 400 mV so as to adhere satisfactorily to negatively charged keratinous materials. One example of a natural intervening coating is an aqueous-containing solution containing 0.1 wt. % grape seed extract. The coating, when dried, carries a cationic charge.

Any of the coating compositions may contain compatible actives, such as conditioning and/or rejuvenating ingredients. Benefits of conditioning ingredients include added shine, but also flexibility and moisture which, for example, when included in mascara, help keep eyelashes, pliable and less likely to dry out and break. Conditioning ingredients in mascara contribute to a more even mascara application, since when eyelashes are conditioned, the surfaces are smoother. The smoother surfaces help pigment in mascara to adhere more evenly to eyelashes. Some of these conditioning agents may be moisturizers which penetrate hairs along the lashline, making them softer. Other agents, such as humectants, may attract moisture into the eyelashes. Still other agents, for example, proteins or peptides, are said to make the eyelashes stronger by reinforcing fibers that make up the hair strands. Additionally, these proteins and/or peptides may help to plump the eyelashes which is particularly beneficial to those with thin or sparse eyelashes.

Examples of conditioning and/or rejuvenating agents useful in the particulate coatings to promote the health of the eyelashes, may include, but are not limited to, oils, such as argan oil, tea tree oil, jojoba seed oil, avocado oil, and sesame seed oil; humectants, moisturizers and/or lubricants, such as dimethicone, sorbitol, glycerin, polyisobutene, honey derivatives, and sodium hylauronate; Vitamin $B_5$ derivatives, such as panthenol, dexapanthanol, pantethine, lauroyl lysine, hydrolyzed keratin, and hydrolyzed wheat protein.

In addition to pigment, e.g. iron oxides, which may be contained in or associated with, untreated particulates, pigment also may be trapped in any of the coatings, that is, the initial cationic coating, the film former finish, or any intervening coatings, to intensify color and promote volume.

In accordance with the compositions and methods of the present invention, particulates, such as fibers or powders, suitable for treatment according to the present invention, may be made of various materials, naturally-derived, semi-synthetic and/or synthetic. As naturally-derived particulates, mention may be made of, for example, cellulose, and cellulose-based materials, including, but not limited to, cellulose (and) magnesium stearate, cotton, linen, and so forth. Also useful is polylactic acid, a thermoplastic aliphatic polyester derived from corn starch, tapioca or sugar cane. Also suitable as particulate matter for use in the present invention would be a semi-synthetic material such as rayon, a manufactured and regenerated cellulose fiber. Synthetic particles may include, but are not limited to, those made from nylon or polypropylene. Synthetic particulates are said to be particularly useful for imparting volume and length to mascara and eyebrow- and hair-filler products. Synthetic particulates may contain pigments such as carbon black or iron oxides to enhance the overall color effect of products in which they are incorporated.

Fibers useful in carrying out the invention may have a length in the range of from about 1 micrometer to about 4 millimeters and a weight in the range of from about 3 to about 20 denier. Preferably, the fibers are from about 1 millimeter to about 4 millimeters in length, and have a denier in the range of from about 3 to about 15. In certain preferred embodiments of the invention, the fibers have a length in the range of from about 1 millimeter to about 2 millimeters, and a denier in the range of from about 5 to about 10. The fibers may take any cross-sectional form, such as round, oval, triangular, hexagonal, heart-shaped, star-shaped, and so forth.

One particularly preferred synthetic fiber is composed of nylon-6 (And) iron oxides (And) triethoxycaprylylsilane (And) silica, and is available as NFBL-10D-1R-1MM from Kobo Products, Inc. These fibers are black, have a round cross-section, a length of about 1 millimeter and a denier of about 10. Another preferred synthetic fiber is SPLASH Fiber II 7T-1MM from Kobo Products, Inc. which is composed of nylon-6 (And) silica (And) iron oxides. These fibers have a 7 decitex width (about 6.3 denier), a 1 millimeter length, are charcoal black in color, and have a hexagonal cross-section resulting in a "flower" cross-sectional shape. The greater surface area of these fibers, due to their shape, is also said to offer a more volumizing effect to eyelashes to which the mascara is applied than would typical fibers having a round to oval cross-section, particularly by filling inbetween sparse lashes. Also useful is FDA certified carbon black, 10 denier, 1 mm round nylon fiber (nylon-6 NFCB-10D-1R-1 mm, available from Daito Kasei Kogyo Co. Ltd.).

In accordance with some embodiments of the invention, the particulates are in the form of a fine powder which may take the form of a flake-shaped or plate-like, cellulose product, the flakes having a thickness of about 1 to 2 micrometers and a width of about 8.8 micrometers. Such a powder is available as silk cotton PW fibers, from Kobo Products, Inc.

In some embodiments of the present invention, fibers having various cross-sectional shapes, lengths and deniers may be blended, with or without powders particulates, in compositions of the present invention to achieve customized formulations for a desired effect; that is, enhanced volume and/or length, when applied to keratinous materials.

In accordance with the present invention, a method of coating particles comprises encapsulating the particles with at least one cationically charged material, for example a cationic polymer, optionally followed by coating with a water-soluble polymeric film finish coating to further seal the cationically charged coating to the particle surfaces. In some embodiments of the invention, the particulates are coated with one or more additional coats of cationic or anionic material or a combination thereof, the net cationic charge of the final dried particulates falling within a range of from about 0.1 mV to about 400 mV. One skilled in the art would appreciate that any method which will coat the particulates may be used as long as the treated particulates retain a net catonic charge in the range of from about 0.1 mV to about 400 mV.

One known method of coating or encapsulating particles, for example, fibers, is spray coating. Fibers are introduced into a reactor or microfluidizer which acts like a vortex. Air is pumped into a chamber of the fluidizer from the bottom cauising the fibers to fly around. The volume of air flow (i.e., flap) is controlled to prevent the light weight fibers from clogging the fluidizer filter. Thereafter, a solution, a dispersion, or an aqueous-containing emulsion, of a spray formulation containing a cationically charged material is introduced into the microfluidizer, and the circulating fibers are coated with the cationically-charged solution. The spray composition is sprayed by one or more nozzles situated in various regions of the microfluidizer. Typically for each spraying operation, the pressure used may be in the range of from about 1.5 to about 3.5 bar, such as about 2.5 bar, and the pump speed will vary depending on the viscosity of the spray formulation. The pump speed may be, for example, in the range of from about 2.5 to about 30 rpm, such as from about 5 to about 10 rpm. As an example of this type of process, particles, such as fibers or powder particulates, to be coated are stirred by a gas stream which also ensures their drying (i.e., the evaporation of the organic solvent and/or water). This method involves at least one coating, but may include successive coatings, of the fibers with the spray formulation, followed by at least one drying operation to evaporate off the organic solvent and/or water.

The cationically-charged material covalently bonds to the surfaces of naturally-derived particulates carrying surface hydroxyl groups, for example, cellulose-based particulates. On the other hand, the cationically-charged material does not bond to, but coats, synthetic particulates.

Optionally, one or more additional spray formulations, for example, a solution, a dispersion, or an emulsion, containing a film-former material, may be introduced into the fluidizer while air is pumped into the fluidizer chamber, so as to further coat the cationically-charged fibers with the film-former finish material. The twice-coated fibers are then dried again. The film former finish imparts hydrophobicity to the treated fibers. In the case where naturally-derived particulates having surface hydroxyl groups are used, it is particularly useful that the cationically charged particulates receive a film former coating which will render the particulates hydrophobic.

Optionally, one or more additional coatings containing cationic and/or anionic material may be sprayed onto the particulates, prior to the coating with film former, as long as the net final charge of the particulates is cationic and is in the range of from about 0.1 mV to about 400 mV. Each spraying step is followed by a drying step, prior to the final coating with the film former material. The resulting particulates are hydrophobic.

Using confocal microscopy, the inventors have determined ranges of the weight of the coating materials to the weight of the particulates useful in carrying out the spray coating operations. Various ranges were tested, including 0.1:1, 0.25:1, 2.25:1, 3.75:1, 7.25:1, 10:1, 15:1 and 30:1. It was observed that, for use as dry, treated particulates intended for direct application to keratinous material, a useful range of the weight of the solution, dispersion, or emulsion containing the charged coating material to the weight of the particulates in a spray coating operation is in the range of from about 0.1:1 to about 2:1, such as about 0.25:1. A ratio of less than about 0.1:1 is considered undesirable, as such lesser amount would not sufficiently encapsulate the particulates (i.e., the cationic charge would be too low to be useful). The use of a ratio of greater than about 2:1 is also considered undesirable as the additional layers of solution, dispersion or emulsion containing the charged coating material would result in flyaway of the particulates due to the strong charges which begin to repel one another. In the case in which the dried, treated particulates are incorporated into a cosmetic base formula, such as a mascara composition, a broader useful range of the weight of the solution, dispersion, or emulsion containing the charged coating material to the weight of the particulates was observed; the range being from about 0.1:1 to about 5:1, such as about 0.25:1. A useful range of the weight of the solution, dispersion or emulsion containing the film former to the cationically charged particulates is from about 0.1:1 to about 30:1, such as about 3.75:1. A lesser amount of the film former would not be expected to result in dried, sufficiently coated cationically charged particulates. A greater amount of the film former would be too viscous and may result in processing challenges, including clogging the spray apparatus of the microfluidizer. In the case in which the dried, treated particulates are incorporated into a cosmetic base formula, such as a mascara composition, a broader useful range of the weight of the solution, dispersion, or emulsion containing the film former material was observed; the range being about 0.1:1 to about 60:1, such as from about 0.1:1 to about 30:1, for example, about 3.75:1. A lower amount of film former would not be expected to provide sufficient coating to seal the prior coats onto the particulate surfaces and to impart hydrophobicity to the particulates. A greater amount of film former would result in overly tacky particulates which would be expected to agglomerate in the base formula.

Dry, treated particles according to the present invention may be provided in a receptacle including a cap fitted with an applicator of any type, such as a molded or a twisted wire brush, which would be suitable for loading product as it is withdrawn from the receptacle and for depositing the particles on a keratinous surface, including eyelashes, eyebrows or hair. The dry, treated particles may be encapsulated with at least one cationic coating, or with both a cationic coating and a film forming coating, or with at least one cationic coating, one or more additional anionic coatings, and a final film former finish. Cationically-charged fibers encapsulated with the film former are water-resistant.

Compositions of the present invention containing the dry, treated particulates, as described hereinabove, and a suitable vehicle, may also be provided in a receptacle described above for the dry, treated particles per se. Optional ingredients which may be formulated into the compositions may include, but are not limited to, gellants, film formers, pigments, moisturizers, emollients, humectants, preservatives, stabilizers, sequestering agents, and the like.

Treated particulate-containing compositions of the invention may take the form of a mascara which incorporates the basic formulation elements of a conventional mascara. Any type of mascara formulation would be suitable, including aqueous, single oil phase, water-in-oil or oil-in-water emulsions, and emulsions with three or more phases, with particulates dispersed in the oil phase of the emulsions.

Dry, treated particulates prepared according to the present invention may be present in cosmetic formulations in amounts in the range of from about 0.1 to about 4 percent by total weight of the formulation. Preferably, the dry, treated particulates are present in amounts in the range of from about 0.4 to about 4 percent, such as from about 2 to about 4 percent, by total weight of the formulation. Greater than about 4 percent particulates by total weight of the formulation may be expected to result in processing issues, including clogging of equipment, and also non-uniform dispersion in the cosmetic formulation due to agglomeration of the charged particulates.

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. The aqueous phase structuring agent should be compatible with the optically-activated systems, and also compatible with the other ingredients in the formulation. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below. As the optically-activated systems are in water soluble form, an aqueous phase thickening agent also contributes to stabilizing this ingredient in the composition.

Polysaccharides may be suitable aqueous phase thickening agents. Examples of such polysaccharides include naturally derived materials such as agar, agarose, alicaligenes polysaccharides, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

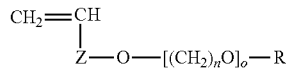

wherein Z is $-(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of $C_{10-30}$ alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

In the event the compositions of the invention are in emulsion form, the composition will comprise an oil phase. Oily ingredients are desirable for the skin moisturizing and protective properties. Oils, if present, will form a barrier on the skin so that the optically-activated complex present in the composition remains on the skin. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin. Volatile oils are more desirable when the skin care products containing the optically-activated complex are being formulated for consumers that have combination or oily skin. The term "combination" with respect to skin type means skin that is oily in some places on the face (such as the T-zone) and normal in others.

Cyclic silicones are one type of volatile silicone that may be used in the composition. Such silicones have the general formula:

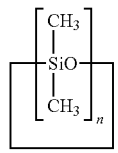

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

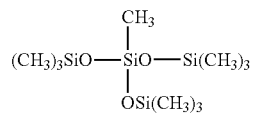

Methyl trimethicone may be purchased from Shin-Etsu Silicones under the tradename TMF-1.5, having a viscosity of 1.5 centistokes at 25° C.

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

Suitable esters are mono-, di-, and triesters. The composition may comprise one or more esters selected from the group, or mixtures thereof.

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, -3-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

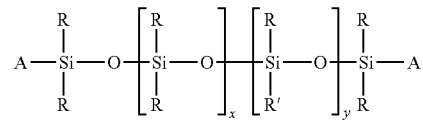

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

Various types of fluorinated oils may also be suitable for use in the compositions including but not limited to fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The oil phase structuring agent is compatible with the optically-activated complex, particularly if the optically-activated complex may be solubilized in the nonpolar oils forming the oil phase of the composition. The term "compatible" means that the oil phase structuring agent and optically-activated complex are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to the following.

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety. It is particularly desirable to incorporate silicone elastomers into the compositions of the invention because they provide excellent "feel" to the composition, are very stable in cosmetic formulations, and relatively inexpensive.

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula:

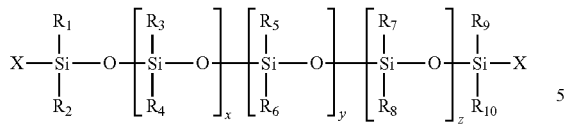

wherein $R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

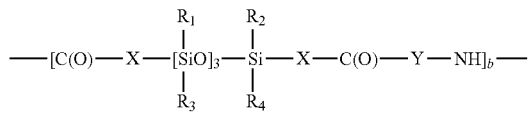

wherein X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

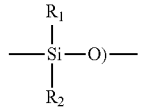

and Y is:
(a) a linear or branched alkylene having from about 1-40 carbon atoms which may be substituted with:
(i) one or more amide groups having the general formula $R_1CONR_1$, or
(ii) $C_{5-6}$ cyclic ring, or
(iii) phenylene which may be substituted with one or more $C_{1-10}$ alkyl groups, or
(iv) hydroxy, or
(v) $C_{3-8}$ cycloalkane, or
(vi) $C_{1-20}$ alkyl which may be substituted with one or more hydroxy groups, or
(vii) $C_{1-10}$ alkyl amines; or
(b) $TR_5R_6R_7$ wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

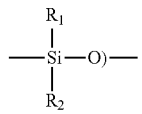

Preferred is where $R_1$, $R_2$, $R_3$, and $R_4$ are $C_{1-10}$, preferably methyl; and X and Y is a linear or branched alkylene. Preferred are silicone polyamides having the general formula:

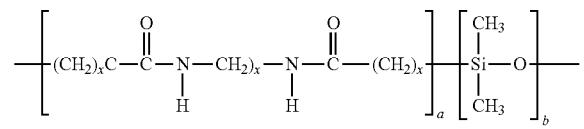

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

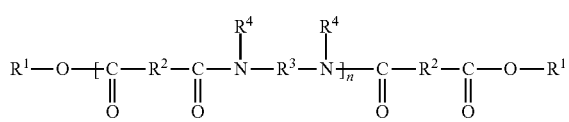

wherein n denotes a number of amide units such that the number of ester groups ranges from about 10% to 50% of the total number of ester and amide groups; each $R^1$ is independently an alkyl or alkenyl group containing at least 4 carbon atoms; each $R^2$ is independently a $C_{4-42}$ hydrocarbon group, with the proviso that at least 50% of the $R^2$ groups are a C30-42 hydrocarbon; each $R^3$ is independently an organic group containing at least 2 carbon atoms, hydrogen atoms and optionally one or more oxygen or nitrogen atoms; and each $R^4$ is independently a hydrogen atom, a $C_{1-10}$ alkyl group or a direct bond to $R^3$ or to another $R^4$, such that the nitrogen atom to which $R^3$ and $R^4$ are both attached forms part of a heterocyclic structure defined by $R^4$—N—$R^3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

Also suitable as the oil phase structuring agent may be one or more natural or synthetic waxes such as animal, vegetable, or mineral waxes. Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Suitable silicone surfactants include polyorganosiloxane polymers that have amphiphilic properties, for example contain hydrophilic radicals and lipophilic radicals. These silicone surfactants may be liquids or solids at room temperature.

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

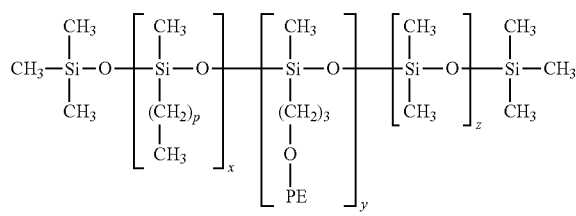

wherein p is 0-40 (the range including all numbers between and subranges such as 2, 3, 4, 13, 14, 15, 16, 17, 18, etc.), and PE is $(-C_2H_4O)_n-(-C_3H_6O)_b$—H wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. Nos. 5,236,986 and 5,412,004, 5,837,793 and 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011. One preferred crosslinked silicone elastomer emulsifier is dimethicone/PEG-10/15 crosspolymer, which provides excellent aesthetics due to its elastomeric backbone, but also surfactancy properties.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula:

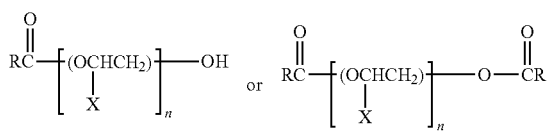

where RCO is the carboxylic ester radical, X is hydrogen or lower alkyl, and n is the number of polymerized alkoxy groups. In the case of the diesters, the two RCO-groups do not need to be identical. Preferably, R is a C6-30 straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

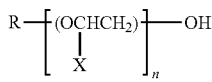

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, *camelina sativa* seed oil, *boswellia serrata* extract, olive extract, *Aribodopsis Thaliana* extract, *Acacia Dealbata* extract, *Acer Saccharinum* (sugar maple), acidopholus, acorus, *aesculus, agaricus*, agave, agrimonia, algae, aloe, citrus, *brassica*, cinnamon, orange, apple, blueberry, cranberry, peach, pear, lemon, lime, pea, seaweed, caffeine, green tea, chamomile, willowbark, mulberry, poppy, whey protein, and those set forth on pages 1646 through 1660 of the CTFA Cosmetic Ingredient Handbook, Eighth Edition, Volume 2. Further specific examples include, but are not limited to, *Camelia sinensis, Siegesbeckia orientalis, Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientalis, Fructus Mume, Ascophyllum Nodosum, Bifida* Ferment lysate, *Saccharomyces* lysate, *Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata* Peel, *Punica Granatum, Asparagopsis, Curcuma Longa, Menyanthes Trifoliata, Helianthus Annuus, Triticum vulgare, Hordeum Vulgare, Cucumis Sativus, Evernia Prunastri, Evernia Furfuracea*, and mixtures thereof.

It may also be desirable to include one or more sunscreens in the compositions of the invention. Such sunscreens include chemical UVA or UVB sunscreens or physical sunscreens in the particulate form. Inclusion of sunscreens in the compositions containing the optically-activated complex will provide additional protection to skin during daylight hours.

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

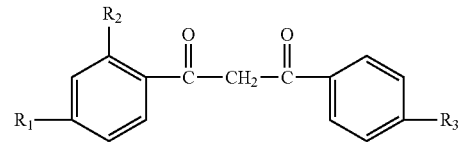

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4' diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

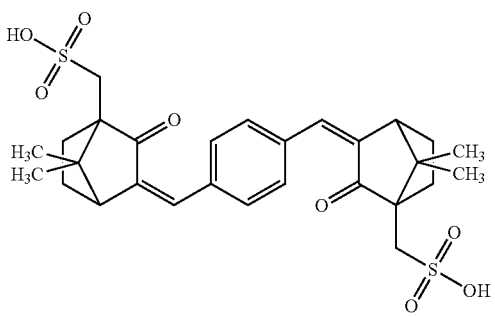 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

UVB sunscreens may also be employed in the systems of the present invention. The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

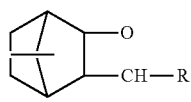

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

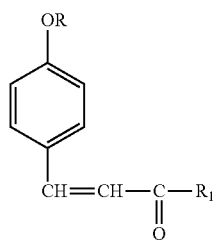

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

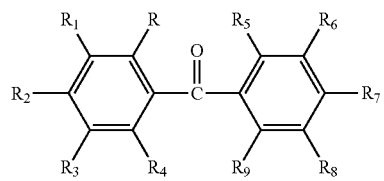

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

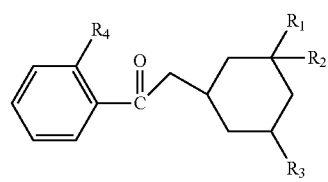

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

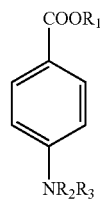

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula:

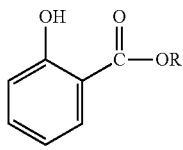

wherein R is a straight or branched chain alkyl, including derivatives of the above compound formed from mono-, di-, or triethanolamines. Particular preferred are octyl salicylate, TEA-salicylate, DEA-salicylate, and mixtures thereof. Generally, the amount of the UVB chemical sunscreen present may range from about 0.001-45%, preferably 0.005-40%, more preferably about 0.01-35% by weight of the total composition.

A particularly preferred sunscreen agent is including bisiminomethylguaiacol manganese chloride, in view of its cationic charge.

If desired, the compositions of the invention may be formulated to have a certain SPF (sun protective factor) values ranging from about 1-50, preferably about 2-45, most preferably about 5-30. Calculation of SPF values is well known in the art.

The compositions of the invention may contain particulate materials in addition to the optically reflective materials, including other pigments, inert particulates, or mixtures thereof. Suggested ranges for all particulate materials is from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored (for example, white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, calcium aluminum borosilicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable. Some embodiments contain melanin.

The composition may contain 0.001-8%, preferably 0.01-6%, more preferably 0.05-5% by weight of the total composition of preservatives. A variety of preservatives are suitable, including benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, hexylene glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In certain preferred embodiments, the composition contains ethylhexyl glycerin or phenoxyethanol/chlorphenesin/glycerin/sorbic acid. In one preferred embodiment the composition is free of parabens.

The compositions of the invention may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are retinyl palmitate, retinol. retinoic acid, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on. In one preferred embodiment, the composition contains pentaerythrityl tetra-di butyl hydroxyhydrocinnamate.

Embodiments herein further comprises treating skin for improvement by applying to the skin the compositions of the invention. The systems may be applied in the forms mentioned herein, as part of skin care regimens. For example, the system may be applied to the skin alone, or incorporated into a day cream. The systems may be applied after cleansing the skin. The systems may be applied to the skin under or over skin care products, such as foundations or other color cosmetics or incorporated into such skin care products.

Dry, treated particulates described herein may be applied to clean, dry eyelashes after application of a coating of conventional mascara, or between applications of conventional mascara. Formulations according to the present invention may take a variety of forms. The formulation may be a mascara composition which is similar to a conventional mascara but which contains fibers treated according to embodiments herein; that is, fibers provided with a cationic coating, and, optionally, with a further coating containing film former and, with or without one or more intermediate coatings between the initial cationic coating and the film former. One or more coats of the mascara containing fibers treated according to the invention may be applied to the eyelashes to increase volume and length of the lashes, depending on the user's needs. The formulation also may take the form of a pigmented or unpigmented waxy- or gel-based composition containing the cationically-coated fibers in a hydrophilic carrier, such as water and alcohol. The latter formulation may be applied to clean, dry eyelashes to provide enhanced volume and length, optionally followed by the application of a conventional mascara. Or, the waxy- or gel-based formula may be applied between coats of conventional mascara. Formulations according to the present invention will not only enhance the volume and length of eyelashes of the user, but, due to the presence of the charged fibers, will result in wear which is superior to that achievable with fiber-containing conventional products. It will be apparent to those of skill in the art that the formulations of the invention also may be used as a brow or hair filler.

The following examples further illustrate various specific embodiments described herein, without limiting the broad scope thereof.

EXAMPLES

Example 1—Preparation of Treated Fibers

Procedure:
1. 150 gms. of Splash Fiber II 7T 1 mm fibers (available from Kobo Products, Inc.) were introduced into the fluid bed of a microfluidizer (Glatt Air Techniques, model no. GPCG-1).
2. Fibers were fluidized at 25% flap with the temperature set to 60° C.
3. 150 gms. of a cationically charged solution containing 15 wt. % polyquaternium-6, 70 wt. % water and 15 wt. % denatured alcohol was top sprayed from the lower port of the fluidizer at 2.5 bar atomizing air pressure & 30 rpm pump speed over a period of about 19 minutes. To minimize clumping of fibers, spraying was paused twice to allow the fibers to dry and start flowing again.
4. Fibers were allowed to dry for 35 min with 60° C. inlet air. Levelling off of the product temperature for 10 minutes, followed by increasing temperature, signalled that the moisture had been removed.
5. 60 gms. of a film-former solution containing hydrophobic silicones as follows: 52.19 wt. % methyl trimethicone, 35.4 wt. % trimethylsilicate and 12.41 wt. % dimethicone was top sprayed, from the lower port of the at 2.5 bar atomizing air pressure & 30 rpm pump speed over a period of about 7 minutes.
6. Fibers were allowed to dry for 15 minutes with 60° C. inlet air.
7. Confocal analysis confirmed that the fibers were completed coated.

Example 2—Attraction of Hair to Treated Fibers

Procedure:
1. First and second hair swatches, weighing 1.36 gms. and 1.68 gms., respectively were introduced into separate vessels containing either control fibers ((nylon-6 (and) black iron oxide (and) silica, available as SPLASH FIBER II 7T-2MM, from Kobo Products, Inc.) or coated fibers prepared as in Example 1.
2. After about 2 minutes, each of the hair swatches was removed from the respective vessels and re-weighed.
Result:
It was observed that the swatch introduced into the vessel containing the control fibers still weighed 1.36 gms., while the hair swatch introduced into the vessel containing the treated fibers weighed 1.70 gms. indicating that the hair swatch attracted 0.02 gms of treated fibers.

Example 3—Preparation of Treated Fibers

Procedure:
1. 300 gms. of Silk Cotton PW fibers (available from Kobo Products, Inc.) were introduced into the fluid bed fo a microfluidizer.
2. Fibers were fluidized at 25% flap with the temperature set to 20° C.
3. 300 g of a cationically charged solution containing 15 wt. % poly quaternium-6, 70 wt. % water and 15 wt. % denatured alcohol was top sprayed from the lower port of the fluidizer at 2.5 bar atomizing air pressure & 30 rpm pump speed over a continuous period of about 40 minutes.
4. Fibers were permitted to dry for 50 minutes with 60° C. inlet air. Levelling off of the product temperature for 10 minutes, followed by increasing temperature, signalled that the moisture had been removed.
5. 300 gms. of a dispersion of hydrophilic film-former, polyurethane-35 in water (41 wt. % polyurethane in water, available as Baycusan C 1004 from Covestro) was top sprayed, from the lower port of the fluidizer, at 2.5 bar atomizing air pressure & 30 rpm pump speed over a period of 38 minutes.
6. Fibers were dried for 50 minutes with 60° C. inlet air.
7. Confocal analysis confirmed that the fibers were completed coated.

Example 4—Dispersibility of Fibers in Water

Procedure:
1. 5 gms of each of the treated Silk Cotton PW fibers of Example 3, Silk Cotton PW fibers coated only with the cationically charged material used in Example 3, and untreated control Silk Cotton PW fibers, were dispersed in separate vessels, each containing 50 ml water.
2. After 10 minutes, it was observed that the twice-coated Silk Cotton PW fibers presented as two phases; the hydrophobic fibers not being water-dispersible, floated to the top of the water. The fibers receiving only the cationically charged coating were partially dispersible, some fibers settling to the bottom of the vessel. The control fibers, absorbing water, settled to the bottom of the vessel.

Example 5—Preparation of Treated Fibers

Procedure:
1. 200 gms. of Splash Fiber II 7T 1 mm were introduced into the fluid bed of a fluidizer.
2. Fibers were fluidized at 25% flap with the temperature set to 20° C.
3. 100 gms. of a cationically charged solution containing 15 wt. % poly quaternium-6, 70 wt. % water and 15 wt. % denatured alcohol was top sprayed from the lower port of the fluidizer at 2.5 bar atomizing air pressure & 30 rpm pump speed until fibers were observed to clump and fluidization was lost.

4. Fibers were dried for 15 minutes with inlet air at 60° C. to drive off sufficient moisture until fluidization resumed. Inlet air remained on for the remainder of the process.

5. An additional 100 gms. of the cationically charged solution containing 15 wt. % poly quaternium-6, 70 wt. % water and 15 wt. % denatured alcohol was top sprayed from the lower port of the fluidizer at 2.5 bar atomizing air pressure & 30 rpm pump speed until fibers were observed to clump and fluization was lost.

6. The fibers then were dried at 60° C. with inlet air for 50 minutes.

7. 200 gms. of of a dispersion of hydrophilic film-former, polyurethane-35, in water (available from Covestro as Baycusan C 1004—was top sprayed, from the lower port of the fluidizer, at 2.5 bar atomizing air pressure & 30 rpm pump speed over a period of 20 minutes with no significant clumping observed.

8. Fibers were dried at 60° C. for 50 minutes.

9. Confocal analysis confirmed that the fibers were completed coated.

Example 6—Preparation of Treated Fibers

Procedure:

1. 100 gms of NFBL-10D-1R ((nylon-6 (and) iron oxides (and) triethoxycapryl silane (and) silica, available from Kobo Products, Inc.)) was introduced into the bed of a fluidizer.

2. Fibers were fluidized at 25% flap with the temperature set to 20° C.

3. 100 gms. of a cationically charged solution containing 15 wt. % poly quaternium-6, 70 wt. % water and 15 wt. % denatured alcohol was top sprayed from the lower port of the fluidizer at 2.5 bar atomizing air pressure & 10 rpm pump speed until fibers were observed to clump and fluidization was lost.

4. Fibers were dried for 15 minutes with inlet air at 60° C. to drive off sufficient moisture until fluidization resumed. Inlet air remained on for the remainder of the process.

5. 100 gms. of a film-former solution containing a mixture of 59.46 wt. % trisiloxane, 20.27 wt. % dimethicone and 20.27 wt. % trimethylsiloxysilicate was top sprayed, from the lower port of the fluidizer, at 2.5 bar atomizing air pressure & 5 rpm pump speed over a period of 20 minutes with no significant clumping observed.

6. Fibers were dried at 60° C. for 50 minutes.

7. Confocal analysis confirmed that the fibers were completed coated. The zeta potential (measured by Brookhaven Instruments, model NanoBrook Omni 28001, spectrophotometer) of the treated fibers was determined to be 143 mV.

Example 7—Preparation of Treated Fibers

Procedure:

Example 6 was repeated except that the film-former solution contained a mixture of 59.1 wt. % trisiloxane, 18.43 wt. % dimethicone, 21.87 wt. % trimethylsiloxysilicate and 0.6 wt. % polyglyceryl-3 siloxane dimethicone.

Example 8—Preparation of Treated Fibers

Procedure:

Example 6 was repeated except that the fibers were sprayed with 25 wt. % of a cationically charged solution contained 15 wt. % polyquaternium-6, 70 wt. % water and 15 wt. % denatured alcohol. The cationically charged fibers were sprayed with 5 wt. % of a film former solution contained 59.46 wt. % trisiloxane, 20.27 wt. % dimethicone, and 20.27 wt. % trimethylsiloxysilicate. The zeta potential of the treated fibers was determined to be 79 mV.

Example 9—Preparation of Treated Fibers

Procedure:

Example 8 was repeated except that the cationically charged fibers were sprayed with 7.5 wt. % of a film former solution containing 59.46 wt. % trisiloxane, 20.27 wt. % dimethicone and 20.27 wt. % trimethylsiloxysilicate. The zeta portential of the treated fibers was determined to be 59 mV.

Example 10—Preparation of Treated Fibers

Procedure:

Example 8 was repeated except that the cationicaly charged fibers were sprayed with 3.75 wt. % of a film former solution containing 59.46 wt. % trisiloxane, 20.27 wt. % dimethicone and 20.27 wt. % trimethylsiloxysilicate.

Example 11—Preparation of Treated Fibers

Procedure:

The process of Example 6 was repeated except that an intermediate coating of 0.1 weight percent aqueous solution of grapeseed extract was sprayed on the cationically coated fibers prior to coating with the film former solution.

Example 12—Preparation of Treated Fibers

Procedure:

The process of Example 6 was repeated except that the initial cationic coating contained 0.2 gms powdered iron (FeO) in a watery gel containing 60.7 wt. % water, 0.1 wt. % hydroxyethylcellulose and 39 wt. %.

Example 13—Gel-based Treated Fiber-Containing Formulation

| Sequence | Ingredients | Weight Percent |
|---|---|---|
| 1 | water | 59.70 |
| 1 | ammonium acryloyldimethyltaurate/beheneth-25 methacrylate crosspolymer | 1.50 |
| 1 | sodium dehydroacetate | 0.50 |
| 1 | disodium EDTA | 0.05 |
| 1 | sodium benzoate | 0.05 |
| 2 | black iron oxide/calcium alginate/calcium chloride/sodium chloride | 9.00 |
| 3 | glycerine | 4.00 |
| 4 | polyurethane-35/water | 20.00 |
| 5 | phenoxyethanol | 0.80 |
| 5 | *treated fibers | 4.00 |
| 5 | silica | 0.40 |
| | TOTAL | 100.00 |

*prepared in Example 5

Procedure:
1. Sequence 1 ingredients were mixed in main beaker with agitation at 35° C. for one hour.
2. Sequence 2 ingredient was added to the main beaker and the batch mixed with a homogenizer at room temperature for 20 minutes.
3. Sequence 3 and sequence 4 ingredients were added to the main beaker and the batch mixed with the homogenizer for 10 minutes.
4. Sequence 5 ingredients were added to the main beaker and the batch mixed with the homogenizer for 10 minutes.

Example 14—Mascara Formulation Containing Treated Fibers

| Sequence | Ingredients | Weight Percent |
|---|---|---|
| 1 | water | 17.8799 |
| 1 | hydroxyethylcellulose | 0.4000 |
| 2 | water | 1.0000 |
| 2 | aminomethyl propanediol | 0.2500 |
| 3 | water | 10.0000 |
| 3 | hydroxyethylcellulose | 0.1000 |
| 4 | isostearic acid | 0.2500 |
| 5 | iron oxides | 10.0000 |
| 5 | *treated fibers | 2.0000 |
| 6 | water | 2.0000 |
| 7 | polyvinylpyrrolidone | 0.8000 |
| 7 | calcium aluminum borosilicate | 0.1000 |
| 7 | sodium dehydroacetate | 0.2000 |
| 7 | silica | 4.9000 |
| 7 | disodium EDTA | 0.1000 |
| 8 | pantethine | 0.0300 |
| 8 | panthenol | 0.0300 |
| 8 | melanin | 0.0100 |
| 9 | water | 1.0000 |
| 9 | dimethicone | 0.1000 |
| 10 | isostearic acid | 0.3500 |
| 10 | pentaerythrityl tetra-di butyl hydroxyhydrocinnamate | 0.0500 |
| 10 | stearic acid | 6.6000 |
| 10 | carnauba | 7.3500 |
| 10 | glyceryl stearate | 5.7000 |
| 10 | polyisobutene | 5.7000 |
| 10 | lauroyl lysine | 0.0100 |
| 10 | vinylpyrrolidone/eicosene copolymer | 1.5000 |
| 11 | water | 1.2000 |
| 12 | water | 2.7000 |
| 12 | aminomethyl propanediol | 1.3500 |
| 13 | water | 3.0000 |
| 13 | acacia Senegal gum | 0.2500 |
| 14 | dimethicone PEG-8 polyacrylate | 3.0000 |
| 15 | water/acrylates copolymer | 7.0000 |
| 16 | water | 1.1940 |
| 16 | sodium hyaluronate | 0.0060 |
| 17 | water/hydrolyzed wheat protein | 0.0001 |
| 17 | phenoxyethanol/chlorphenesin/glycerin/sorbic acid | 1.3000 |
| 18 | ethylhexylglycerin | 0.5000 |
| | TOTAL | 100.0000 |

*prepared in Example 10

Procedure:
1. Sequence 1 ingredients were mixed in main beaker with mixing at 45° C. for 20 minutes.
2. Sequence 2 ingredients were added to a separate beaker and mixed with propeller at room temperature until dissolved.
3. Sequence 3 ingredients were added to a separate beaker and mixed with prop at 45° C. for 20 minutes.
4. Sequence 3, 4 and 5 ingredients were added to a separate beaker and homogenized for 20 minutes at room temperature.
5. The ingredients of steps 2 and 4 were added to the main beaker with mixing.
6. Sequence 6 and 7 ingredients were mixed in a separate beaker until dissolved at room temperature, and were then added to the main beaker.
7. Sequence 8 ingredients were added to the main beaker, and the main beaker heated to 85° C. while mixing for 5 minutes.
8. Sequence 9 ingredients were added to the main beaker while maintaining beaker temperature at 85° C. with mixing for 5 minutes.
9. Sequence 10 ingredients were added to a separate beaker while heating to 90° C. with propeller mixing until uniform.
10. The batch of step 9 was pour slowly into the main beaker to avoid air entrapment while homogeneous mixing and maintaining temperature of main beaker between 85-90° C.
11. Sequence 11 ingredient was used to rinse beaker containing residual Sequence 10 ingredients.
12. Sequence 12 ingredients were mixed at room temperature until dissolved and clear and then were added to the main beaker.
13. Sequence 13 ingredients were mixed until uniform and then added to the main beaker.
14. Sequence 14 ingredient was added to the main beaker with mixing.
15. Sequence 15 ingredient was added to the main beaker with mixing.
16. Sequence 16 ingredients were mixed until uniform and then the mixture was added to the main beaker.
17. Sequence 17 ingredients were added individually to the main beaker, while mixing for 5 minutes.
18. Sequence 18 ingredient was added to the main beaker with continuous mixing for 10 minutes.

Example 15—Evaluation of Treated Fibers by Confocal Microscopy

Procedure:
A.
1. 0.02 wt. % fluorescein sodium salt was added to 99.98 wt. % of a cationic coating solution comprising 15 wt. % polyquaternium-6, 70 wt. % water and 15 wt. % alcohol. The solution was used to spray coat 100 gms NFBL-10D 1R fibers in a microfluidizer according to the procedures described hereinabove.
2. To evaluate the uniformity of the coating on the fibers, 0.02 gm samples of the coated fibers were examined under a confocal microscope with transmission light (about 300 nm) and laser light (about 488 nm), respectively. Under laser light, it was observed that the entire peripheral surfaces of every fiber fluoresced indicating that each fiber was fully encapsulated with the cationic coating. No fluorescence was observed under transmission light.
B.
1. Step A1 was repeated.
2. The cationically coated fibers were then subjected to a spray coating containing 3 wt. % of a silicone blend (52.19 wt. % methyltrimethicone, 35.4 wt. % trimethylsiloxysilicate and 12.41 wt. % dimethicone).
3. To evaluate the uniformity of the cationic coating on the fibers, and to ascertain whether the silicone blend would permit or block illumination of the fluorescein, 0.02 gm samples of the coated fibers were examined under a confocal microscope with transmission light and with laser light, respectively. It was observed that the entire peripheral surface of each fiber fluoresced under the laser light indicating that the cationic coating remained uniform.

C.
1. Step A1 was repeated.
2. The cationically coated fibers were washed 20 times, for 30 minutes each time, in water at 3000 rpm in a centrifuge and then dried in an incubator overnight at 50° C.
3. To evaluate the uniformity of the cationic coating on the fibers, 0.02 gm samples of the cationically coated fibers were examined under a confocal microscope with transmission light and with laser light, respectively. Under laser light, it was confirmed that all of the cationic coating had been removed from the fibers, as observed by the lack of fluorescence.

D.
1. Steps C 1 and 2 were repeated except that the cationically coated fibers were washed only once, and dried.
2. The washed fibers were then spray coated with a 3 wt. % of a silicone blend containing 52.19 wt. % methyltrimethicone, 35.4 wt. % trimethylsiloxysilicate and 12.41 wt. % dimethicone.
3. The fibers of step 2 were then washed 20 times, and then dried, as described above.
4. To evaluate the uniformity of the cationic coating on the fibers, 0.02 gm samples of the cationically coated fibers were examined under a confocal microscope with transmission light and with laser light, respectively. The observation of the illumination of the entire periphery of each fiber under laser light confirmed that each fiber remained fully coated with the cationic material. The silicone coating not only sealed the cationic coating to the fibers but also rendered the fibers water-resistant.

Figure 2:
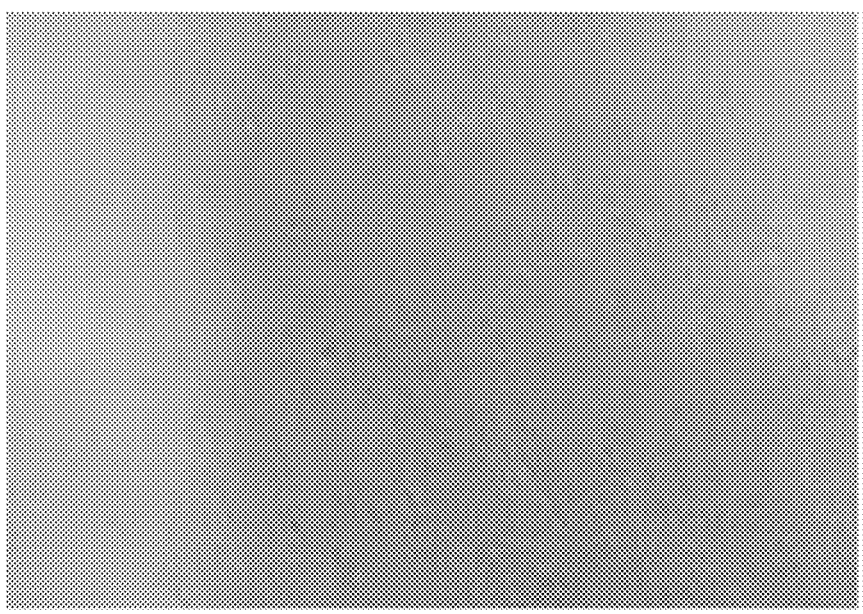
FIG. 2 depicts a blank sheet of paper onto which film-former coated, cationically-charged fibers have not been released from a brush withdrawn from a vial of the charged fibers.

Example 16—Virgin (Non-Charged) Fibers and Film-Former-Coated Cationically Charged Fibers 1. 1-2 grams of virgin fibers (nylon-6: NFCB-10D-1R 1 mm—nylon fiber/FDA certified carbon black/10 denier/1 mm/round, available from Daito Kasei Kogyo Co. Ltd.) were loosely packed, using a spatula, into a tube equipped with a wiper, and the tube was secured with a cap fitted with a brush. 1-2 grams of cationically-charged fibers (nylon-6: NFCB-10D-1R 1 mm—nylon fiber/FDA certified carbon black/10 denier/1 mm/round, obtained from Daito Kasei Kogyo Co. Ltd., subsequently encapsulated with polyquaternium-6, and then further treated with a hydrophilic film-former coating of dimethicone and trimethylsiloxysilicate/polyglyceryl-3 siloxane dimethicone in trisiloxane were loosely packed, using a spatula, into a separate tube equipped with a wiper, and the tube was secured with a cap fitted with a brush.
2. The respective caps were then removed from each of the tubes, the brush in each tube, loaded with fibers, being withdrawn through the wiper, over separate blank sheets of white paper.
3. FIG. 1 shows fibers scattered over the initially blank white paper. Virgin fibers carry no charge of their own; however, as the brush loaded with fibers was withdrawn from the tube, through the wiper, the friction produced by the brush moving through the wiper caused the brush to be statically (i.e., relatively negatively) charged. The previously uncharged virgin fibers captured in the bristles of the brush also became negatively charged by attracting negative charges from the atmosphere. The statically charged fibers repelled one another as well as the brush. It was further observed that the brush could not be fully inserted back into the tube after being withdrawn. Prior to the brush being withdrawn, the fibers were loosely entangled about one another around the brush in the tube. Inserting the negatively charged brush back into the tube through the wiper caused the entangled fibers to be compacted in the bottom of the tube so that the brush could not be reloaded with fibers.
4. FIG. 2 depicts a blank sheet of paper, since the film-former coated, cationically charged fibers according to the invention, did not scatter from the brush onto the paper as the brush was withdrawn from the tube, but remained entrapped in the bristles of the brush. Although the friction caused by the brush moving through the wiper caused the brush to be statically (i.e., relatively negative) charged, and although the film-former coated, cationically-charged fibers according to the invention also picked up negative charges from the atmosphere, the positive and negative charges on the fibers briefly canceled each other out. As a result, the fibers did not repel one another. As the static charge on the fibers dissipated, the positively charged fibers adhered to the negatively charged brush. The brush was easily re-inserted into the tube because the coated, cationically charged fibers in the tube did not agglomerate or compact.

Figure 3:
FIG. 3 is a photograph showing the scattering of statically-charged fibers under the right eye after the in the range of from about 0.1 mV to about 400 mV fibers were applied to mascara-coated eyelashes, and further showing no scattering of film-former coated, cationically-charged fibers under the left eye after the film-former coated, cationically-charged fibers were applied to mascara-coated eyelashes.
Figure 4:
FIG. 4 is a photograph of the right eye area taken one hour after the initial application of statically-charged fibers to mascara-coated eyelashes followed by wiping the undereye are clean of fallen fibers.
Figure 5:
FIG. 5 is a photograph of the left eye area taken one hour after the initial application of film-former coated, cationically-charged fibers to mascara-coated eyelashes followed by wiping the undereye area clean.

Example 17—Virgin (Uncharged) Fibers and Coated, Cationically Charged Fibers Applied to Lashes 1. Separate tubes of loosely packed virgin fibers and film-former coated, cationically-charged fibers were provided as indicated in Example 16.
2. A panelist applied a first coat of a commercial (non-waterproof) mascara to the lashes of both eyes.
3. The panelist immediately thereafter applied the virgin fibers to the mascara-coated lashes of the right eye, using the brush applicator, while the mascara was still tacky. The panelist then applied the film former-coated, cationically-charged fibers, using the brush applicator, onto the lashes of the left eye while the mascara was still tacky. The panelist noted that the virgin fibers were difficult to apply and began to fall to the cheek during application. As shown in FIG. 3, while some fibers adhered to the lashes, fibers also flew about and about 90 fibers were counted on the skin of the right cheek and the right side of the nose. On the other hand, the coated, cationically-charged fibers were smoothly and easily applied, and adhered well to the lashes. As discussed above in Example 16, while the virgin fibers carried static charges which caused them to repel one another and neither adhere well to the brush or to the lashes, the positively charged fibers of the invention adhered to the brush carrying the static (i.e., negative) charges and to the negatively charges lashes.
4. Any fallen fibers were then wiped clean from both undereye areas including the cheek and the nose.
5. One hour after the initial applications of fibers to the mascara-coated lashes, about 30 virgin fibers were observed on the skin of the cheek under the right eye, as shown in FIG. 4. Additionally, eye irritation was reported. In contrast, the film-former coated, cationically-charged fibers of the invention remained adhered to the lashes. Only two fibers were observed to have fallen on the undereye area of the left eye, as shown in FIG. 5.

Increasing the Charge of the Treated Fibers

As noted previously, cationically charged particulates adhere to negatively charged keratinous materials, such as lashes or hair. The cationic charge of the treated particulates described herein can further be increased when used with certain applicators and containers. It is important to have an optimal cationic charge on the fibers. If the charge on the fibers is too high (i.e., over 65 mV), the fibers would repel each other, which could result in insufficient amount deposited on the lashes. If the charge on the fibers is too low (i.e., below 3 mV), the attraction between the cationic fibers and the negatively charged lashes would be inadequate for the fibers to adhere to the lashes, which could result in insufficient volume as fewer fibers would adhere to the lashes.

Figure 6:
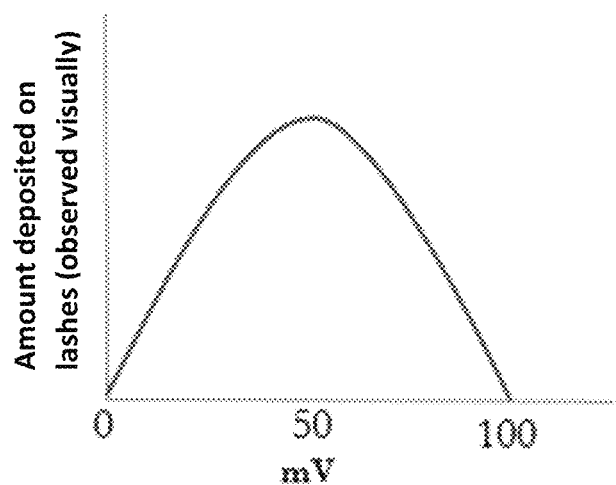
FIG. 6 is a graph showing the amount of treated fibers deposited on lashes (observed visually) as a function of charge of the treated fibers.

The amount of treated fibers deposited on lashes (observed visually) as a function of charge is shown in FIG. 6. As shown in FIG. 6, the amount of fibers deposited on the lashes increases as a function of charge, but only up until approximately 50 my to 65 mV, and the amount of fibers deposited decreases thereafter.

Advantageously, embodiments herein provide for optimal adherence benefits by treating particulates as described herein to result in a cationic charge in the range of 3 mV to 65 mV, thereby providing for maximized deposit of treated particulates on lashes through attraction between the cationically charged particulates and the negatively charged lashes.

In various embodiments, the treated fibers described in the examples above can be placed into a container (e.g. a mascara bottle) and applied with an applicator (e.g., a mascara wand). When the mascara wand, which has picked up some of the treated fibers, makes contact with the mascara wiper in the bottle, a static charge is generated by the friction. The static charge is then transferred to the fibers, thereby increasing the cationic charge of the treated fibers on the mascara wand. The mascara wand or applicator may be made of a thermoplastic (or synthetic) polymer, for example, but not limited to polypropylene, polyoxymethylene, and combinations thereof. The mascara bottle and/or wiper may be made of polyethylene.

The following examples illustrate the increase in cationic charge to the treated fibers using a mascara wand and wiper. While a mascara wand and wiper were used in the example below, other containers and applicators may be used. The control used is untreated fiber. The fibers were treated as described in Example 18 below.

Example 18—Preparation of Treated Fibers

Procedure:
1. 100 gms of NFBL-10D-1R fibers was introduced into the bed of a fluidizer.
2. Fibers were fluidized at 25% flap with the temperature set to 20° C.
3. 100 gms. of a cationically charged solution containing 15 wt. % poly quaternium-6, 78 wt. % water and 7 wt. % denatured alcohol was top sprayed from the lower port of the fluidizer at 2.5 bar atomizing air pressure & 10 rpm pump speed until fibers were observed to clump and fluidization was lost.
4. Fibers were dried for 15 minutes with inlet air at 60° C. to drive off sufficient moisture until fluidization resumed. Inlet air remained on for the remainder of the process.
5. 100 gms. of a film-former solution containing a mixture of 90.3 wt. % dimethicone, 9.44 wt. % trimethylsiloxysilicate, and 0.26 wt. % polyglyceryl-3 siloxane dimethicone was top sprayed, from the lower port of the fluidizer, at 2.5 bar atomizing air pressure & 5 rpm pump speed over a period of 20 minutes with no significant clumping observed.
6. Fibers were dried at 60° C. for 50 minutes.

The fibers were treated according to Example 18 above and placed into a polyethylene container, a polypropylene wand was then inserted into the container of treated fibers. The wand, which picked up some of the treated fibers, was then pulled out of the container and rubbed or wiped against the wiper portion of the container at least once. The tables below show results of five, fifteen, and forty frictions (e.g., rubbing or contacting the mascara wand against the mascara wiper), but fewer or more frictions may be performed.

The control (untreated fibers) contains approximately 1.5 g of neat fibers and the treated fibers contains approximately 2.4 g of coated fibers. Both samples were placed into the same component type for ease of comparison. Approximately 0.3 g of fibers was taken for the Zeta potential evaluation each time. Each sample was ran three times to obtain the average. A Zeta Potential & Particle Size Analyzer from Brookhaven Instrument Model #: Nano Brook Omni was used in the analysis.

TABLE 1

Untreated fibers, initial charge

| Sample ID | Zeta Potential (mV) |
|---|---|
| Sample 1 | −4.26 |
| Sample 2 | −9.81 |
| Sample 3 | −5.18 |
| Mean: | −6.42 |
| Standard Error: | 1.72 |
| Standard Deviation: | 2.97 |

TABLE 2

Control after 5 frictions

| Sample ID | Zeta Potential (mV) |
|---|---|
| Sample 1 | −6.25 |
| Sample 2 | 3.64 |
| Sample 3 | −3.24 |
| Mean: | −1.95 |
| Standard Error: | 2.93 |
| Standard Deviation: | 5.07 |

TABLE 3

Untreated fibers, charge after 15 frictions

| Sample ID | Zeta Potential (mV) |
|---|---|
| Sample 1 | 3.48 |
| Sample 2 | 5.24 |
| Sample 3 | 0.56 |
| Mean: | 3.09 |
| Standard Error: | 1.37 |
| Standard Deviation: | 2.37 |

TABLE 4

Control after 40 frictions

| Sample ID | Zeta Potential (mV) |
|---|---|
| Sample 1 | −2.65 |
| Sample 2 | −4.73 |
| Sample 3 | 3.99 |
| Mean: | −1.13 |
| Standard Error: | 2.63 |
| Standard Deviation: | 4.55 |

TABLE 5

Fibers treated according to Example 18, initial charge

| Sample ID | Zeta Potential (mV) |
|---|---|
| Sample 1 | 8.10 |
| Sample 2 | 2.07 |
| Sample 3 | 8.97 |
| Mean: | 6.38 |
| Standard Error: | 2.17 |
| Standard Deviation: | 3.76 |

TABLE 6

Fibers treated according to Example 18, charge after 5 frictions

| Sample ID | Zeta Potential (mV) |
|---|---|
| Sample 1 | 18.75 |
| Sample 2 | 29.15 |
| Sample 3 | 24.23 |
| Mean: | 24.04 |
| Standard Error: | 3.01 |
| Standard Deviation: | 5.21 |

TABLE 7

Fibers treated according to Example 18, charge after 15 frictions

| Sample ID | Zeta Potential (mV) |
|---|---|
| Sample 1 | 28.78 |
| Sample 2 | 27.85 |
| Sample 3 | 28.66 |
| Mean: | 28.43 |
| Standard Error: | 0.29 |
| Standard Deviation: | 0.50 |

TABLE 8

Fibers treated according to Example 18, charge after 40 frictions

| Sample ID | Zeta Potential (mV) |
|---|---|
| Sample 1 | 24.59 |
| Sample 2 | 33.69 |
| Sample 3 | 27.75 |
| Mean: | 28.68 |
| Standard Error: | 2.67 |
| Standard Deviation: | 4.62 |

As shown in the tables above, the average initial static charge of the neat or untreated fibers is −6.42 mV and the average initial static charge of the treated fibers is 6.38 mV. After five frictions (e.g., five times of rubbing the rod against the wiper), the control showed an average increase in the static charge to −1.95 mV and the average static charge of the treated fibers increased to 24.04 mV. After fifteen frictions, the average static charge of the control and the treated fibers increased to 3.09 mV and 28.43 mV. After forty frictions, the average static charge for the control decreased to −1.13 mV, whereas the treated fibers show an increase in the average static charge to 28.68 mV.

As evidenced by the results, the untreated fibers possess a negative charge (anionic charge) initially. After friction, the static charge starts to build up after five frictions and fifteen frictions. However, after forty frictions, the charge of the untreated fibers drops back down to negative and the untreated fibers were unable to retain a cationic charge. In contrast, the fibers treated according to the methods described herein possess a positive (cationic) charge initially, and the positive charge builds up and increases with successive frictions. Accordingly, the results in Tables 1-8 above show that particulates treated according to methods described herein retain more cationic charge than untreated particulates.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method of maintaining a cationic charge of treated particulates, comprising:
   coating a rod with the cationically-charged particulates;
   contacting the rod with a surface at least once to generate a static charge; and
   transferring the static charge to the cationically-charged particulates on contact with the surface,
   wherein the cationic charge is positive, and
   wherein the cationic charge increases with successive friction of the rod against a mascara wiper from which the rod is successively withdrawn, and
   wherein the cationically-charged particulates comprise particulates encapsulated in a first coating comprising a first material, and in a second, outer coating comprising a second material, the first coating comprising a cationically-charged material in an amount sufficient to impart a cationic charge in the range of from about 0.1 mV to about 400 mV to the particulates, and the second coating comprising a film former material in an amount sufficient to render the particulates hydrophobic, wherein a weight ratio of the cationically-charged material to the particulates is in the range of from about 0.1:1 to about 5:1.

2. The method of claim 1, wherein the rod comprises a thermoplastic polymer.

3. The method of claim 2, wherein the thermoplastic polymer is selected from the group consisting of polypropylene, polyoxymethylene, and combinations thereof.

4. The method of claim 1, wherein the static charge generated is in the range of 3 mV to 65 mv.

5. The method of claim 1, wherein contacting the rod with the cationically-charged particulates comprises inserting the rod into a composition comprising the cationically-charged particulates.

6. The method of claim 5, wherein the composition is in the form of a mascara, a brow filler or a hair filler.

7. The method of claim 5, wherein the composition is aqueous, a dispersion or an emulsion.

8. The method of claim 1, wherein the rod is a mascara wand and the surface is the mascara wiper.

9. The method of claim 8, wherein contacting the rod with the surface comprises wiping the mascara wand against the mascara wiper to generate the static charge.

10. The method of claim 8, wherein the mascara wiper comprises polyethylene.

11. The method of claim 1, wherein the second, outer coating comprises a film former material comprising a silicone, an acrylates polymer, an acrylates copolymer, a polyvinylpyrrolidone (PVP) derivative, a polyurethane, a polyvinyl amine, a polyvinyl acetate, sucrose acetate isobutyrate, or a combination of any two or more thereof.

12. The method of claim 1, wherein the cationically-charged material comprises a naturally-derived or a synthetic cationic polymer.

13. The method of claim 12, wherein the synthetic cationic polymer comprises polyquaternium-4, polyquaternium-5, polyquaternium-6, polyquaternium-10, polyquaternium-39, polyquaternium-44, polyquaternium-46, distearyldimonium chloride, cinnamidopropyltrimonium chloride, cetrimonium chloride, guar hydroxypropyltrimonium chloride, or a combination of any two or more thereof.

14. The method of claim 12, wherein the naturally-derived cationic polymer comprises a cationically charge-modified derivative of one or more of guar gum, cellulose, a protein, a polypeptide, chitosan, lanolin, or a starch.

15. The method of claim 12, wherein the particulates are in the form of synthetic powder particulates, synthetic fibers, or a combination thereof.

* * * * *